(12) United States Patent
Pant

(10) Patent No.: US 9,958,325 B2
(45) Date of Patent: May 1, 2018

(54) MULTI-SCAN OPTICAL SYSTEM

(71) Applicant: Metal Power Analytical (I) Pvt. Ltd., Mumbai (IN)

(72) Inventor: Priyadarshan Divyadarshan Pant, Mumbai (IN)

(73) Assignee: Metal Power Analytical (I) Pvt. Ltd., Mumbai (IN)

( * ) Notice: Subject to any disclaimer, the term of this patent is extended or adjusted under 35 U.S.C. 154(b) by 0 days. days.

(21) Appl. No.: 15/624,008

(22) Filed: Jun. 15, 2017

(65) Prior Publication Data

US 2017/0363471 A1 Dec. 21, 2017

(30) Foreign Application Priority Data

Jun. 21, 2016 (IN) .............................. 201621021316

(51) Int. Cl.
| | |
|---|---|
| *G01J 3/28* | (2006.01) |
| *G01J 3/06* | (2006.01) |
| *G01J 3/02* | (2006.01) |
| *G01J 3/04* | (2006.01) |
| *G01J 3/443* | (2006.01) |
| *G01N 21/31* | (2006.01) |
| *G01N 21/33* | (2006.01) |
| *G01J 3/18* | (2006.01) |
| *G01J 3/32* | (2006.01) |

(52) U.S. Cl.
CPC ............... *G01J 3/06* (2013.01); *G01J 3/0218* (2013.01); *G01J 3/0232* (2013.01); *G01J 3/04* (2013.01); *G01J 3/18* (2013.01); *G01J 3/2803* (2013.01); *G01J 3/32* (2013.01); *G01J 3/443* (2013.01); *G01N 21/3103* (2013.01); *G01N 21/33* (2013.01); *G01J 2003/045* (2013.01); *G01J 2003/061* (2013.01); *G01J 2003/065* (2013.01); *G01J 2003/282* (2013.01); *G01N 2201/0826* (2013.01)

(58) Field of Classification Search
CPC ........ G01J 3/02; G01J 3/28; G01J 3/06; G01J 3/04; G01J 3/44; G01J 3/18; G01J 3/32; G01N 21/33; G01N 21/31
See application file for complete search history.

(56) References Cited

U.S. PATENT DOCUMENTS 5,734,485 A * 3/1998 Buchkremer ............ G03H 1/24
359/1

* cited by examiner

*Primary Examiner* — Abdullahi Nur
(74) *Attorney, Agent, or Firm* — Blueshift IP, LLC; Robert Plotkin

(57) ABSTRACT

The present disclosure relates to the field of optical systems. The envisaged multi-scan optical system is compact and stable. The system comprises an excitation source, a hydra fiber cable, a wavelength selector, an optical element, and a detector. The excitation source is configured to emit composite light. The hydra fiber cable has a head and a plurality of tentacles, and is configured to receive the composite light via a second lens. The plurality of tentacles is configured to emit the composite light towards the wavelength selector which includes a plurality of optical slits (s1-s8) and a plurality of shutters. The wavelength selector is configured to selectively collect and filter the composite light directed by a first lens and the plurality of tentacles by means of the plurality of shutters. The detector is configured to detect the plurality of spectral line scans reflected by the optical element for spectrometric analysis.

10 Claims, 1 Drawing Sheet

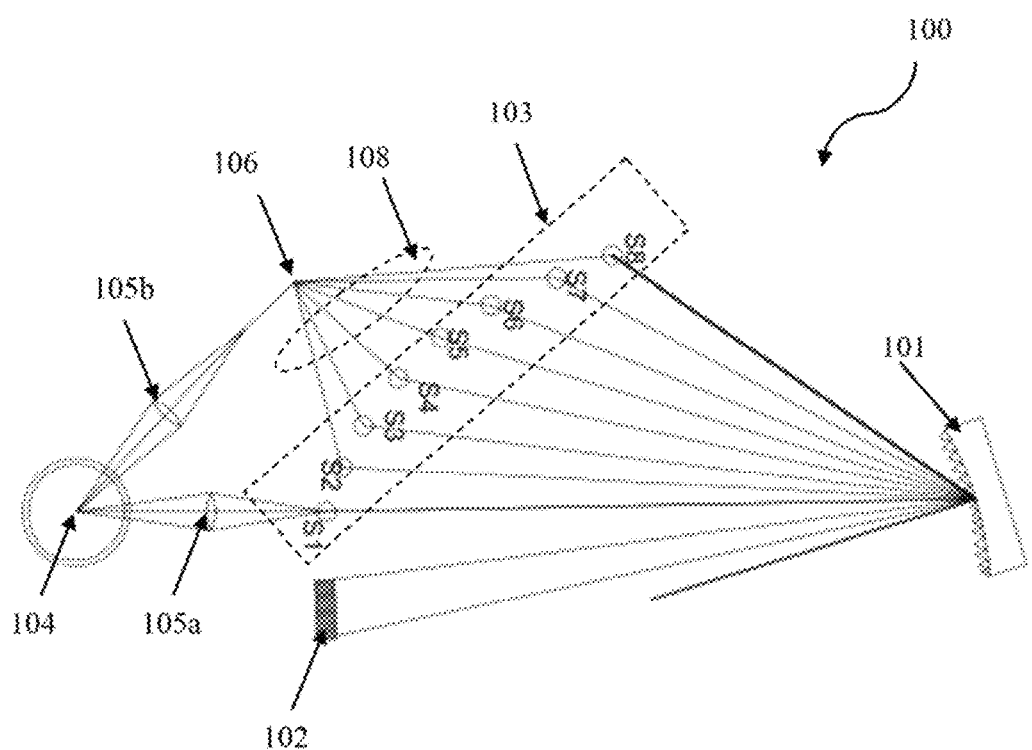

MULTI-SCAN OPTICAL SYSTEM

FIELD

The present disclosure relates to the field of optical systems.

BACKGROUND

Conventionally, the optical systems used in an atomic emission spectrometer include an excitation source, a plurality of lenses, a wavelength selector, and a plurality of detectors. Typically, the wavelength selector is a single slit configuration. The use of single slit based wavelength selector reduces the stability of the conventional optical system. Further, the wavelength selector is configured to direct the composite light towards the plurality of detectors. Each of the plurality of detector is tuned to capture the diffracted composite light of a particular wavelength. Typically, these detectors are charge coupled devices. However, the use of multiple charge coupled devices increases the cost of the optical system.

Therefore, there is felt a need for a multi-scan optical system that alleviates the above-mentioned drawbacks of the conventional optical system.

OBJECTS

Some of the objects of the present disclosure, which at least one embodiment herein satisfies, are as follows:

It is an object of the present disclosure to ameliorate one or more problems of the prior art or to at least provide a useful alternative.

An object of the present disclosure is to provide a multi-scan optical system which facilitates coverage of different wavelength ranges using a single detector across multiple scans separated across time periods.

Another object of the present disclosure is to provide a multi-scan optical system which requires fewer detectors to facilitate increased wavelength range coverage for a given resolution.

Still another object of the present disclosure is to provide a multi-scan optical system which facilitates increased effective resolution as compared to the conventional single-scan CCD systems.

Yet another object of the present disclosure is to provide a multi-scan optical system that provides compact and stable optics.

Still another object of the present disclosure is to provide a multi-scan optical system that is cost effective.

Other objects and advantages of the present disclosure will be more apparent from the following description, which is not intended to limit the scope of the present disclosure.

SUMMARY

The present invention envisages a multi-scan optical system. The system comprises an excitation source, a hydra fiber cable, a wavelength selector, an optical element, and a detector. The excitation source is configured to emit composite light. The hydra fiber cable is disposed downstream of the excitation source. The hydra fiber cable has a head and a plurality of tentacles configured at the ends of the hydra fiber cable respectively. The head is configured to collect the composite light emitted by the excitation source via a second lens. The plurality of tentacles is configured to multiplex the composite light collected by the head, and is further configured to transmit multiple composite lights. The wavelength selector includes a plurality of optical slits (s1-s8).

The wavelength selector is configured to selectively collect and filter the composite light directed by a first lens and the multiple composite lights transmitted by the plurality of tentacles. The wavelength selector is further configured to direct a plurality of spectral line scans, of different wavelengths, corresponding to each of the plurality of optical slits. In an embodiment, the wavelength selector includes a plurality of shutters configured to sequentially select at least one optical slit (s1-s8). The plurality of shutters is operated pneumatically or electrically.

The detector is configured to detect the plurality of spectral line scans reflected by an optical element for spectrometric analysis. In an embodiment, the optical element is a concave holographic diffractive reflection grating. In another embodiment, the detector is a charge coupled device.

In an embodiment, the first lens and the second lens are configured to direct the composite light received from the excitation source towards a first slit (s1), of the plurality of slits (s1-s8), and the hydra fiber cable respectively.

In an embodiment, the excitation source is selected from the group consisting of an inductively coupled plasma, a direct current plasma, and a microwave induced plasma.

In another embodiment, the first lens and the second lens are spark light collection lens respectively.

In still another embodiment, each of the plurality of spectral line scans is associated with respective incident angle. In yet another embodiment, the wavelength of the plurality of spectral line scans is in the range of 170 nm to 380 nm.

BRIEF DESCRIPTION OF ACCOMPANYING DRAWING

A multi-scan optical system of the present disclosure will now be described with the help of the accompanying drawing, in which:

FIG. 1 illustrates a schematic view of a multi-scan optical system in accordance with an embodiment of the present disclosure.

LIST OF REFERENCE NUMERALS USED IN DETAILED DESCRIPTION AND DRAWINGS

100—System
101—Optical element
102—Detector
103—Wavelength selector
104—Excitation source
105a—First lens
105b—Second lens
106—Hydra Fiber cable
108—Tentacles

DETAILED DESCRIPTION

Conventionally, the optical systems used in an atomic emission spectrometer include an excitation source, a plurality of lenses, a wavelength selector, and a plurality of detectors. Typically, the wavelength selector is a single slit configuration. The use of single slit based wavelength selector reduces the stability of the conventional optical system. Further, the wavelength selector is configured to direct the composite light towards the plurality of detectors. Each of the plurality of detector is tuned to capture the diffracted composite light of a particular wavelength. Typically, these detectors are charge coupled devices. However, the use of multiple charge coupled devices increases the cost of the optical system.

The system of the present disclosure is now described with reference to FIG. 1. FIG. 1 illustrates a schematic view of the multi-scan optical system 100 in accordance with an embodiment of the present disclosure.

The present invention envisages a multi-scan optical system 100. The system 100 comprises an excitation source 104, a hydra fiber cable 106, a wavelength selector 103, an optical element 101, and a detector 102. The excitation source 104 is configured to emit composite light. The hydra fiber cable 106 is disposed downstream of the excitation source 104. The hydra fiber cable 106 has a head (not shown in FIGURE) and a plurality of tentacles 108 configured on the ends of the hydra fiber cable 106 respectively. The head is configured to collect the composite light emitted by the excitation source 104 via a second lens 105b. The plurality of tentacles 108 is configured to multiplex the composite light collected by the head of the hydra fiber cable 106, and is further configured to transmit multiple composite lights towards the wavelength selector.

The wavelength selector 103 includes a plurality of optical slits (s1-s8). The wavelength selector 103 is configured to selectively collect and filter the composite light directed by a first lens 105a and the multiple composite lights transmitted by the plurality of tentacles 108. The wavelength selector 103 is further configured to direct a plurality of spectral line scans, of different wavelengths, corresponding to each of the plurality of optical slits (s1-s8). In an embodiment, the wavelength selector 103 includes a plurality of shutters (not shown in FIGURE) configured to sequentially select at least one optical slit (s1-s8). The plurality of shutters is operated pneumatically or electrically. In an embodiment, each of the plurality of spectral line scans is associated with respective incident angle.

In an embodiment, the excitation source 104 is a plasma spark source. Typically, the plasma spark source employs an inductively coupled plasma to produce excited atoms and ions that emit electromagnetic radiation at wavelengths having characteristic of a particular element to be analyzed. In one embodiment, the excitation source 104 is selected from the group consisting of inductively coupled plasma, direct current plasma, and microwave induced plasma.

In another embodiment, the optical element 101 is a concave holographic diffractive reflection grating.

In another embodiment, the first lens 105a and the second lens 105b are a spark light collection lens. The first lens 105a is adapted to collect composite light from the excitation source 104. Further, the first lens 105a is configured to direct the collected composite light towards a first slit (s1).

The second lens 105b is adapted to collect composite light from the excitation source 104. Further, the second lens 105b is configured to direct the collected composite light towards the hydra fiber cable 106.

In an embodiment, at least one slit (s2 to s8) is selected from the group consisting of a second slit (s2), a third slit (s3), a fourth slit (s4), a fifth slit (s5), a sixth slit (s6), a seventh slit (s7), and an eight slit (s8). In an embodiment, the hydra fiber cable 106 is a single stemmed fiber with a head on one side/tail end and the plurality of tentacles on the other side. This design enables usage of multiple incident angles (two or more) per detector to ensure different incident angles and therefore coverage of different wavelength ranges using the same detector across multiple scans separated across time periods.

The detector 102 is configured to detect the plurality of spectral line scans reflected by the optical element 101 for spectrometric analysis. In an embodiment, the detector 102 is a charge coupled device (CCD).

In accordance with an embodiment of the present disclosure, the system 100 provides eight scans wherein each scan is associated with respective incident angle to provide wavelength selection. Although the present disclosure is described using eight scans, the system 100 of the present disclosure can be used with any number of scans subject to at least two scans. In an embodiment, the wavelength of the plurality of spectral line scans is in the range of 170 nm to 380 nm.

In an embodiment, in a first scan (switching), the composite light from the excitation source 104 is incident on the first slit (s1). The first slit (s1) is adapted to pass a first spectral line scan of the composite light. The first spectral line scan is directed towards the optical element 101. The optical element 101 is configured to diffract the first spectral line scan towards the detector 102. The detector 102 is configured to capture and detect the first spectral line scan. Typically, the diffracted first spectral line scan has a wavelength in the range of 170 nm to 200 nm.

In another embodiment, in a second scan (switching), the composite light from the excitation source 104 is incident on the second slit (s2). The second slit (s2) is adapted to pass a second spectral line scan of the composite light. The second spectral line scan is directed towards the optical element 101. The optical element 101 is configured to diffract the second spectral line scan towards the detector 102. The detector 102 may be configured to capture and detect the second spectral line scan. Typically, the diffracted second spectral line scan has a wavelength in the range of 201 nm to 230 nm.

In still another embodiment, in a third scan (switching), the composite light from the excitation source 104 is incident on the third slit (s3). The third slit (s3) is adapted to pass a third spectral line scan of the composite light. The third spectral line scan is directed towards the optical element 101. The optical element 101 is configured to diffract the third spectral line scan towards the detector 102. The detector 102 is configured to capture and detect the third spectral line scan. Typically, the diffracted third spectral line scan has a wavelength in the range of 231 nm to 260 nm.

In yet another embodiment, in a fourth scan (switching), the composite light from the excitation source 104 is incident on the fourth slit (s4). The fourth slit (s4) is adapted to pass a fourth spectral line scan of the composite light. The fourth spectral line scan is directed towards the optical element 101. The optical element 101 is configured to diffract the fourth spectral line scan towards the detector 102. The detector 102 is configured to capture and detect the fourth spectral line scan. Typically, the diffracted fourth spectral line scan has a wavelength in the range of 261 nm to 290 nm.

In an embodiment, in a fifth scan (switching), the composite light from the excitation source 104 is incident on the fifth slit (s5). The fifth slit (s5) is adapted to pass a fifth spectral line scan of the composite light. The fifth spectral line scan is directed towards the optical element 101. The optical element 101 is configured to diffract the fifth spectral line scan towards the detector 102. The detector 102 is configured to capture and detect the fifth spectral line scan. Typically, the diffracted fifth spectral line scan has a wavelength in the range of 291 nm to 320 nm.

In another embodiment, in a sixth scan (switching), the composite light from the excitation source 104 is incident on the sixth slit (s6). The sixth slit (s6) is adapted to pass a sixth spectral line scan of the composite light. The sixth spectral line scan is directed towards the optical element 101. The optical element 101 is configured to diffract the sixth spectral line scan towards the detector 102. The detector 102 is configured to capture and detect the sixth spectral line scan. Typically, the diffracted sixth spectral line scan has a wavelength in the range of 321 nm to 350 nm.

In yet another embodiment, in a seventh scan (switching), the composite light from the excitation source 104 is incident on the seventh slit (s7). The seventh slit (s7) is adapted to pass a seventh spectral line scan of the composite light. The seventh spectral line segment is directed towards the optical element 101. The optical element 101 is configured to diffract the seventh spectral scan line towards the detector 102. The detector 102 is configured to capture and detect the seventh spectral line scan. Typically, the diffracted seventh spectral line scan has a wavelength in the range of 351 nm to 380 nm.

In still another embodiment, in an eighth scan (switching), the composite light from the excitation source 104 is incident on the eighth slit (s8). The eighth slit (s8) is adapted to pass an eighth spectral line scan of the composite light. The eighth spectral line scan is directed towards the optical element 101. The optical element 101 is configured to diffract the eighth spectral line scan towards the detector 102. The detector 102 is configured to capture and detect the eighth spectral line scan. Typically, the diffracted eighth spectral line scan has a wavelength in the range of 351 nm to 380 nm.

The composite light is sequentially passed through each of the plurality of slits (s1 to s8) by controlling the operation of each of the plurality of shutters. In one embodiment, the plurality of shutters is operated pneumatically/electrically in each scan. Further, the operation of the shutters may be controlled sequentially to select the different respective wavelength scans. In an embodiment, the plurality of shutters are configured to control a plurality of tentacles 108, of the hydra fiber cable 106, by keeping one tentacle of the plurality of tentacles 108 active at any point in time and shutting all the other tentacles. Multi-scanning of the light spectrum is done by switching the composite light from one slit (s2 to s8) to another entrance window/slit using the plurality of shutters. This ensures that only a single tentacle of the hydra fiber cable 106 is "active" at any given point in time, as all the other tentacles are blocked by the corresponding shutters.

The optical system of the present disclosure is designed to cover longer wavelength ranges to analyze more spectral lines as required with multiple scanning/switching using the plurality of slits (s1 to s8) through a plurality of tentacles 108 of the hydra fiber cable 106. The wavelength selector 103 is placed downstream of the plurality of tentacles 108 of the hydra fiber cable 106 and the first lens 105a.

In an embodiment, the system 100 of the present disclosure is used with any optical emission spectroscopy.

TECHNICAL ADVANCES AND ECONOMICAL SIGNIFICANCE

The present disclosure described herein above has several technical advantages including, but not limited to, the realization of a multi-scan optical system that:
is cost effective;
makes the optical system more compact;
provides better stability;
increases the resolution; and
increases the wavelength without compromising the resolution.

The disclosure has been described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A multi-scan optical system comprising:
   an excitation source configured to emit composite light;
   a hydra fiber cable disposed downstream of said excitation source, said hydra fiber cable having a head and a plurality of tentacles configured on the ends of said hydra fiber cable respectively, wherein:
   said head is configured to collect the composite light emitted by said excitation source via a second lens; and
   said plurality of tentacles is configured to multiplex the composite light collected by said head, and further configured to transmit multiple composite lights;
   a wavelength selector having a plurality of optical slits (s1-s8), said wavelength selector configured to selectively collect and filter the composite light directed by a first lens and the multiple composite lights transmitted by said plurality of tentacles, and further configured to direct a plurality of spectral line scans, of different wavelengths, corresponding to each of said plurality of slits (s1-s8); and
   a detector configured to detect said plurality of spectral line scans reflected by an optical element for spectrometric analysis.

2. The system as claimed in claim 1, wherein said wavelength selector includes a plurality of shutters configured to sequentially select at least one optical slit (s1-s8).

3. The system as claimed in claim 2, wherein said plurality of shutters is operated pneumatically or electrically.

4. The system as claimed in claim 1, wherein said first lens and said second lens are configured to direct the composite light received from said excitation source towards a first slit (s1), of said plurality of slits (s1-s8), and said hydra fiber cable respectively.

5. The system as claimed in claim 1, wherein said excitation source is selected from the group consisting of an inductively coupled plasma, a direct current plasma, and a microwave induced plasma.

6. The system as claimed in claim 1, wherein said optical element is a concave holographic diffractive reflection grating.

7. The system as claimed in claim 1, wherein said first lens and said second lens are spark light collection lens respectively.

8. The system as claimed in claim 1, wherein each of said plurality of spectral line scans is associated with respective incident angle.

9. The system as claimed in claim 1, wherein said detector is a charge coupled device.

10. The system as claimed in claim 1, wherein the wavelength of said plurality of spectral line scans is in the range of 170 nm to 380 nm.

* * * * *